United States Patent
Liu et al.

(10) Patent No.: US 10,244,612 B2
(45) Date of Patent: Mar. 26, 2019

(54) BULB TUBE PREHEATING

(71) Applicant: SHENYANG NEUSOFT MEDICAL SYSTEMS CO., LTD., Shenyang (CN)

(72) Inventors: Jinjun Liu, Shenyang (CN); Qinghe Song, Shenyang (CN); Qingxiang Shu, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 198 days.

(21) Appl. No.: 15/206,090

(22) Filed: Jul. 8, 2016

(65) Prior Publication Data

US 2017/0094763 A1    Mar. 30, 2017

(30) Foreign Application Priority Data

Sep. 30, 2015 (CN) .......................... 2015 1 0645625

(51) Int. Cl.
  *H05G 1/00* (2006.01)
  *H05G 1/34* (2006.01)
  (Continued)

(52) U.S. Cl.
  CPC .............. *H05G 1/34* (2013.01); *A61B 6/032* (2013.01); *A61B 6/40* (2013.01); *A61B 6/54* (2013.01);
  (Continued)

(58) Field of Classification Search
  CPC ................................... H05G 1/34; H05G 1/36
  See application file for complete search history.

(56) References Cited

U.S. PATENT DOCUMENTS 4,366,575 A    12/1982  Bax
4,775,992 A *  10/1988  Resnick ................... H05G 1/34
                                                        378/109
(Continued)

FOREIGN PATENT DOCUMENTS

BE   1007026 A6   2/1995
CN   1048780 A    1/1991
(Continued)

OTHER PUBLICATIONS

Zhang, Y. et al., "Use and maintenance for a helical CT bulb tube," Chinese Journal of Medical Instrumentation, vol. 28, No. 2, Apr. 30, 2014, 4 pages.
(Continued)

*Primary Examiner* — Dani Fox
(74) *Attorney, Agent, or Firm* — McCoy Russell LLP

(57) ABSTRACT

A method and apparatus for preheating a bulb tube of medical equipment is provided. The method includes: selecting a scanning condition which satisfies an equipment calibration condition, as a preheating condition for the bulb tube, from scanning conditions used by the medical equipment; selecting a new preheating condition if an accumulated thermal capacity according to selected preheating conditions is smaller than a target thermal capacity, until the accumulated thermal capacity reaches the target thermal capacity, wherein the accumulated thermal capacity indicates a sum of a thermal capacity estimated to be generated when the bulb tube is preheated according to the selected preheating conditions, and the target thermal capacity indicates a thermal capacity required to complete the preheating of the bulb tube; preheating the bulb tube according to selected preheating conditions and executing an equipment calibration corresponding to each of the preheating conditions during the bulb tube preheating.

10 Claims, 4 Drawing Sheets

(51) Int. Cl.
*A61B 6/03* (2006.01)
*A61B 6/00* (2006.01)
*H05G 1/36* (2006.01)

(52) U.S. Cl.
CPC ............... *A61B 6/58* (2013.01); *A61B 6/582* (2013.01); *H05G 1/36* (2013.01)

(56) References Cited

U.S. PATENT DOCUMENTS

| | | |
|---|---|---|
| 4,809,311 A | 2/1989 | Arai et al. |
| 4,991,189 A | 2/1991 | Boomgaarden et al. |
| 2008/0152073 A1 | 6/2008 | Fujimoto et al. |
| 2011/0007866 A1 | 1/2011 | Ishikawa et al. |
| 2014/0192961 A1 | 7/2014 | Auernhammer et al. |

FOREIGN PATENT DOCUMENTS

| | | |
|---|---|---|
| CN | 1998271 A | 7/2007 |
| CN | 103494612 A | 1/2014 |
| CN | 103794431 A | 5/2014 |
| CN | 105054959 A | 11/2015 |
| CN | 105232077 A | 1/2016 |
| EP | 0025688 A2 | 3/1981 |
| JP | 2006120548 A | 5/2006 |

OTHER PUBLICATIONS

Zhang, Y. et al., "Use and maintenance for a helical CT bulb tube," Chinese Journal of Medical Instrumentation, vol. 28, No. 2, Apr. 30, 2004, 4 pages.

Chen, S. et al., "Experience on Development of Dedicated CT Scanning Protocol Instead of Tube Preheating," China Academic Journal Electronic Publishing House, Jul. 31, 2005, 4 pages.

\* cited by examiner

BULB TUBE PREHEATING

CROSS-REFERENCE TO RELATED APPLICATIONS

The present application claims priority to Chinese Patent Application No. 2015106456258, filed on Sep. 30, 2015, the entire contents of which are hereby incorporated by reference for all purposes.

BACKGROUND

The present disclosure relates to bulb tube preheating in imaging medical equipment such as Computed Tomography (CT) scanner.

Currently, medical imaging has become a routine diagnostic technique used in hospitals. In the medical equipment used, such as a CT equipment and PET (Positron Emission Tomography)-CT equipment, one of the core components is the bulb tube for generating scanning rays. In operation of this type of the medical equipment, the bulb tube may often be utilized and consumed. For example, the bulb tube may be used in scans and radiation of the equipment or may be used in equipment calibration procedures such as air calibration.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machines, Ultrasound, Positron Emission Tomography (PET), Linear Accelerator (LINAC), and biochemistry analyser. Currently, NMS' products are exported to over 60 countries and regions around the globe, serving more than 5,000 renowned customers. NMS' latest successful developments, such as the 128 Multi-Slice CT Scanner System, Superconducting MRI, LINAC, and PET products, have led China to become a global high-end medical equipment producer. As an integrated supplier with extensive experience in large medical equipment, NMS is committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

Figure 1:
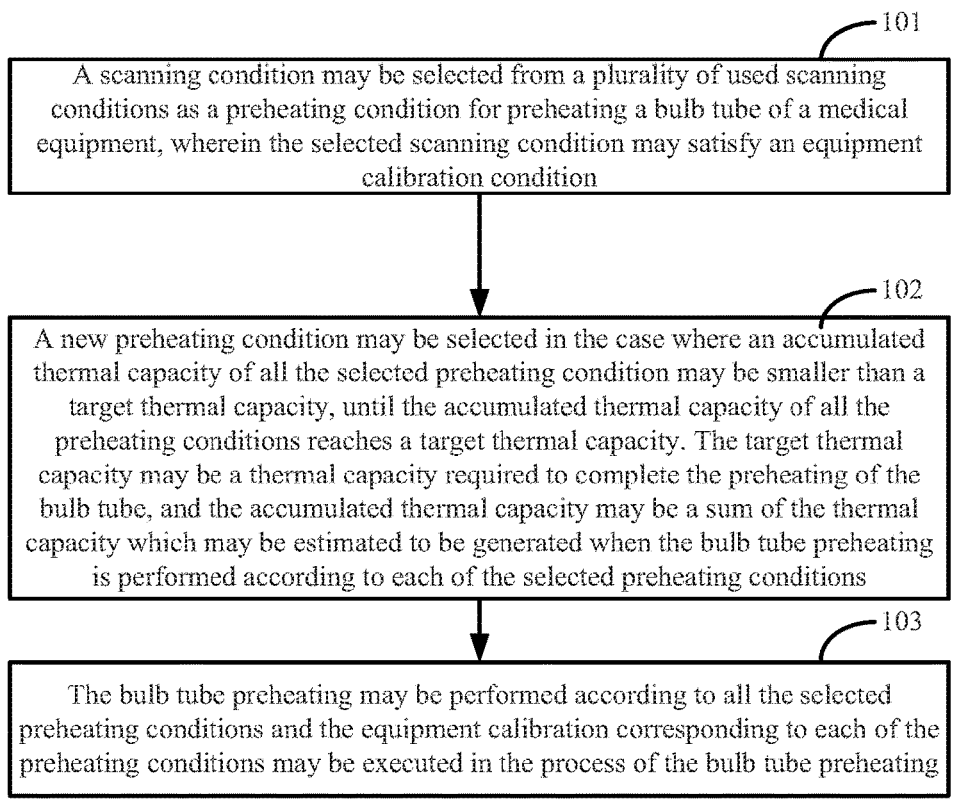
FIG. 1 is a schematic flow chart of a method for preheating a bulb tube according to an example of the present disclosure.

For simplicity and illustrative purposes, the present disclosure is described herein by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Medical diagnostic equipment such as CT equipment may be a commonly used imaging-type medical device which may form images and may be capable of representing morphological features of tissues and organs within a subject to be examined by irradiating X rays to the subject and receiving the X rays penetrating the subject. In the CT equipment, X rays may be generated and emitted by the bulb tube. However, the bulb tube may typically be a core component of higher cost whose lifetime may be prolonged by reducing consumption as much as possible. In this disclosure, a method for preheating a bulb tube is provided which may reduce the consumption of the bulb tube.

According to this method, in one example, "bulb tube preheating" may be combined with "equipment calibration". For example, the equipment calibration may be also completed during the process of preheating the bulb tube.

Through the bulb tube preheating process, the cathode filament of the bulb tube may be heated to accommodate a working state, so as to prevent the filament from easily breaking when suddenly scanning in a cool state. Generally, during the bulb tube preheating, the thermal capacity of the bulb tube may need to reach a set target thermal capacity.

The equipment calibration may include the air calibration, filament current calibration and the like. For example, one reason for the air calibration is that, performances of respective channels of a detector of the imaging-type medical equipment such as the CT equipment, may not be completely identical. Even if intensities of the ray incident onto the respective channels of the detector are completely identical, respective outputs through a preset amplifier may not be completely identical. Therefore, air calibration data may be obtained by running an air calibration program in order to scan the air, and actual scanning data may then be corrected by using the air calibration data while the subject to be examined is scanned, so as to improve image quality. Further, the bulb tube may also be used in the process of the equipment calibration, which may also increase the thermal capacity of the bulb tube.

Since both the bulb tube preheating and the equipment calibration may use the bulb tube and may increase the thermal capacity of the bulb tube, if these two processes are separated and performed independently, it may be equivalent to twice the consumption of the bulb tube. On the other hand, if these two processes are combined, for example, if the thermal capacity of the bulb tube increased by the equipment calibration is used as a part or all of the process of the bulb tube preheating, in other words, if the equipment calibration is performed in the process of the bulb tube preheating, then the consumption of the bulb tube may be appropriately reduced.

Based on the above, FIG. 1 can be referred to for the method for preheating a bulb tube in the example. Taking CT equipment as an example, the method may be performed by a control system of the CT equipment, wherein the control system may control hardware, e.g. a gantry, in which the bulb tube is located. For example, control operation of the gantry may be performed in a control device such as a computer by using control software. After an operation option in the control software for the bulb tube preheating is checked, the control system may instruct relevant hardware devices to perform operations such as the bulb tube preheating or the equipment calibration according to the method illustrated in FIG. 1. The method may include the following steps 101-103.

In the block 101, a scanning condition may be selected from a plurality of used scanning conditions as a preheating condition for preheating the bulb tube of the medical equipment, wherein the selected scanning condition may satisfy an equipment calibration condition.

In the block 102, a new preheating condition may be selected in the case where accumulated thermal capacity of all the selected preheating conditions may be smaller than a target thermal capacity, until the accumulated thermal capacity of all the preheating conditions reaches the target thermal capacity. The target thermal capacity may be a thermal capacity required to complete the bulb tube preheating and the accumulated thermal capacity may be a sum of the thermal capacity which may be estimated to be generated when the bulb tube preheating is performed according to each of the selected preheating conditions.

In the block 103, the bulb tube preheating may be performed according to all the selected preheating conditions and the equipment calibration corresponding to each of the preheating conditions may be executed in the process of the bulb tube preheating.

According to an example, before the bulb tube is preheated, a preheating condition for preheating the bulb tube may be determined first. For example, the preheating condition may include factors such as a voltage or a current obtained when preheating the bulb tube. After the preheating condition is determined, the bulb tube may be preheated according to the voltage and/or the current and the like as defined by the preheating condition. In the flow diagram shown in FIG. 1, the block 101 and the block 102 may be regarded as processes for determining the preheating condition.

Considering that the bulb tube preheating in the example may be combined with the equipment calibration, the scanning condition suitable for the equipment calibration may be selected to perform the bulb tube preheating. The scanning condition for performing the equipment calibration may usually be the scanning condition which may be used, such as the scanning condition which was used when the CT equipment performed scanning of the subject to be examined. In the block 101, the scanning condition which can be used as the preheating condition, may be selected from a plurality of used scanning conditions, and each scanning condition may, for example, include a voltage, focus position, focus size, slice size, fly focus mode, scanning mode and similar conditions used when scanning.

For example, the plurality of used scanning conditions acquired by the CT equipment in the example above may be scanning data of the subject to be examined as recorded by the equipment automatically. For example, after the CT scanning is performed on the subject to be examined by using the CT equipment, the equipment may automatically record information such as the voltage, the focus position, the focus size and the like used by the present scan, as the scanning conditions. According to an example, the scanning conditions may be recorded in an XML file format. A usage count of a certain scanning conditions may also be recorded. For example, if a certain scanning condition is used twice, then the usage count of "2" may also be included in the recorded information on the scanning condition. Furthermore, the CT equipment may also record execution time in which the equipment calibration is performed according to the scanning condition. For example, if the air calibration was performed once according to a certain scanning condition on Jul. 1, 2015, then calibration time of "Jul. 1, 2015" may also be included in the recorded information on the scanning condition. If the air calibration was performed once again on Jul. 6, 2015, then the calibration time in the recorded information on the scanning condition can be updated as "Jul. 6, 2015".

Moreover, a plurality of scanning conditions can be recorded in the CT equipment, the plurality of scanning conditions may include information on different voltages, focus positions, focus sizes, scanning modes and the like, and the information on the usage count and the calibration time and the like may also be different. Assuming ten used scanning conditions are recorded, in the block 101, the scanning conditions which may be used as the preheating conditions may be selected from these ten scanning conditions.

Whether a scanning condition may be selected as a preheating condition may depend on whether it satisfies a specific equipment calibration condition. The equipment calibration may, for example, include the air calibration, the filament current calibration and the like, and the equipment calibration condition may indicate that the corresponding equipment calibration may be performed when specific conditions are reached. Taking the air calibration as an example, the air calibration may be performed on the CT equipment once every 7 days, and the corresponding equipment calibration condition may be that a time interval from the last air calibration exceeds 7 days.

For example, as mentioned above, the execution time of the air calibration, e.g., Jul. 6, 2015, may be included in the information on the scanning conditions recorded by the CT equipment. In the block 101, the latest execution time of the air calibration may be acquired from the recorded information of the scanning conditions. If the time interval from the latest execution time of the air calibration to the current time reaches a pre-set threshold, e.g., 7 days, then it may indicate that the air calibration may need to be performed and the scanning condition may be selected as the preheating condition. The scanning condition may then be selected as the preheating condition, which may mean that at the following bulb tube preheating operation, the bulb tube preheating may be performed by using the modes of the voltage, the focus position and the like in the scanning condition. In fact, the air scanning operation may be performed by using the scanning condition to obtain the corresponding air calibration data. Because the thermal capacity of the bulb tube may be increased in the process of scanning the air according to the scanning condition, it may be equivalent to perform the bulb tube preheating at the same time.

In the block 102, determination of all the preheating conditions may be completed and the number of the preheating conditions may be at least one; wherein, the determination of every preheating condition may be performed in accordance with the block 101. Usually, a plurality of preheating conditions may be needed to be determined in order to reach the target thermal capacity for the bulb tube preheating. For example, the target thermal capacity for the bulb tube preheating may be 20% of the maximum thermal capacity of the bulb tube. However, the time in which the air calibration is performed under one scanning condition may be very short, e.g., 1 second. The thermal capacity of the bulb tube may not be increased much in such a short time. Therefore, it may be needed to perform the air calibration multiple times, and during each calibration process, the thermal capacity of the bulb tube may be increased incrementally and may be accumulated up to the target thermal capacity for the bulb tube preheating.

The CT equipment may determine whether the number of the selected preheating conditions is sufficient by thermal capacity estimation. For example, after two scanning conditions are selected as the preheating conditions, the thermal capacity estimation may be performed according to these two preheating conditions, to estimate how much the thermal capacity of the bulb tube will be increased after the air calibration is performed by using these two scanning conditions. If the estimated accumulated thermal capacity still may not reach the preset target thermal capacity, then a new scanning condition may be selected as a preheating condition. Every time a preheating condition is newly added, it may be estimated whether the accumulated thermal capacity generated according to all the determined preheating conditions may reach the target thermal capacity. If the accumulated thermal capacity may reach the target thermal capacity, then the selection of the preheating condition will be terminated. For example, assuming 8 preheating conditions are selected in total at the termination, it is estimated that the thermal capacity of the bulb tube may be increased to the predetermined target thermal capacity after the air calibration is performed according to these 8 preheating conditions.

After the preheating conditions are determined, in the block 103 the CT equipment may preheat the bulb tube according to the preheating conditions and may execute the corresponding equipment calibration in the process of the bulb tube preheating. For example, assuming the CT equipment has determined 8 preheating conditions, the equipment may then perform the equipment calibration in accordance with these 8 preheating conditions one by one. For example, taking the air calibration as an example, by performing the air calibration according to a scanning condition corresponding to a first preheating condition, the air calibration data corresponding to the scanning condition may be obtained. Subsequently, when the scanning condition is used to perform scanning on the subject to be examined, the air calibration data corresponding to the scanning condition may be used to perform scanning data modification, so as to improve the scanning image quality as much as possible. Then, the air calibration may be performed according to a scanning condition corresponding to a second preheating condition. Each air calibration may also increase the thermal capacity of the bulb tube. Until the execution of the 8 preheating conditions is completed, the target thermal capacity for the bulb tube preheating may be reached. That is, the execution of the 8 preheating conditions may be regarded as the completion of the bulb tube preheating, and in the meantime, the air calibration corresponding to each of the scanning conditions may be executed.

It may be seen from the above example that, according to the method for preheating a bulb tube of the present example, the equipment calibration may be completed at the same time in the process of the bulb tube preheating. That is, two processes of the bulb tube preheating and the equipment calibration may be executed at the same time, which may greatly reduce the consumption of the bulb tube in comparison with a case in which the bulb tube preheating and the equipment calibration are separately executed.

Figure 2:
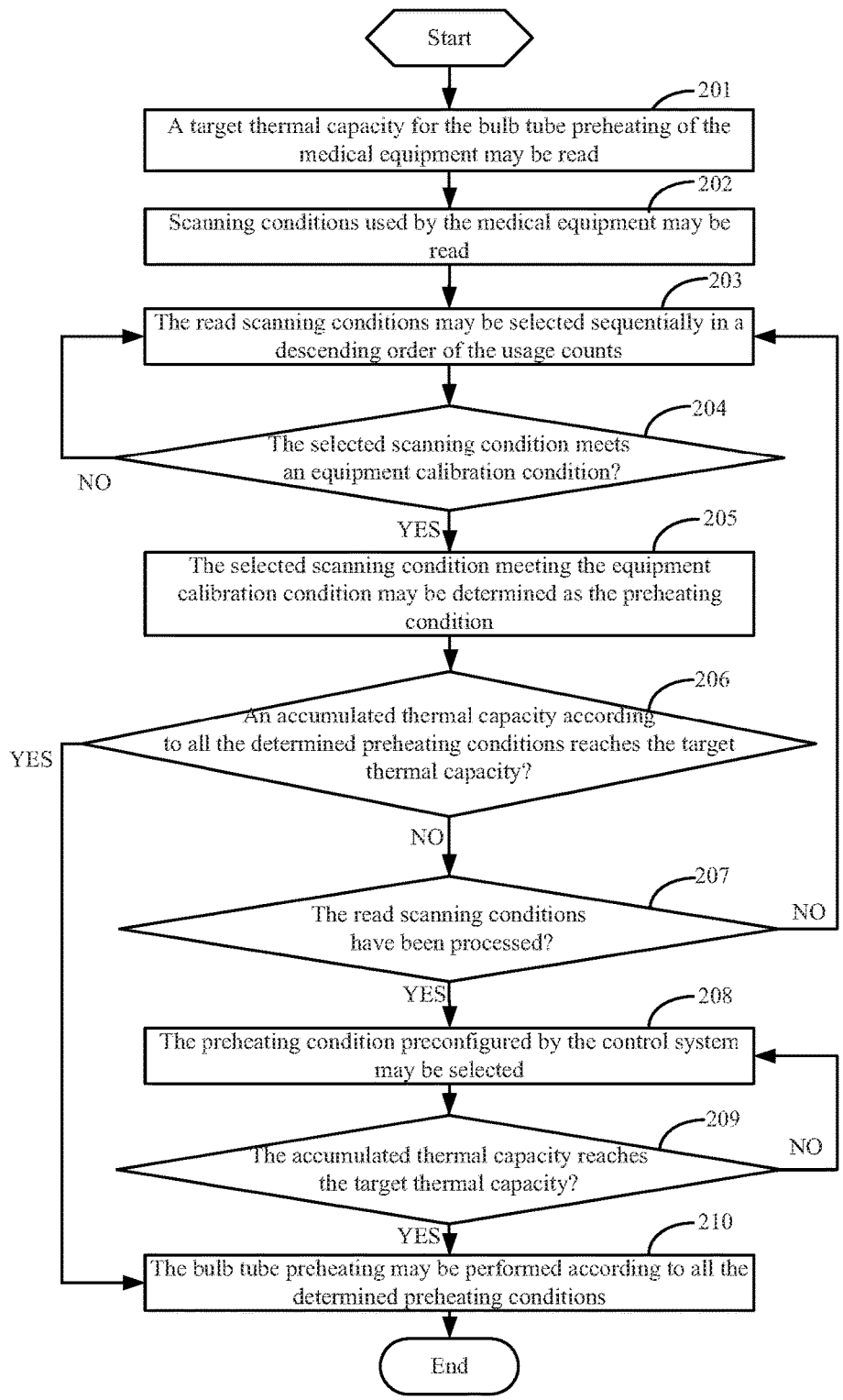
FIG. 2 is a schematic flow chart of a method for preheating a bulb tube according to another example of the present disclosure.

FIG. 2 shows a schematic process flow of a method for preheating a bulb tube according to another example of the present disclosure. According to the method, the blocks which are same as those in the flow illustrated in FIG. 1 will be briefly described in the present example, and the detailed explanation for the flow illustrated in FIG. 1 may be referred to for the details. The difference from the flow illustrated in FIG. 1 may be mainly that, in the present example, when the number of the preheating conditions selected from the recorded used scanning conditions may be insufficient to make the thermal capacity of the bulb tube reach the target thermal capacity for the bulb tube preheating, a preheating condition preconfigured by the control system of the CT equipment may be selected, until the target thermal capacity is reached.

As shown in FIG. 2, by exemplifying the completion of the air calibration during the bulb tube preheating, the method may include the following blocks 201-210.

In the block 201, a target thermal capacity for the bulb tube preheating of the medical equipment may be read.

For example, the target thermal capacity may be n % of the maximum thermal capacity of the bulb tube, and n may be 20.

In the block 202, scanning conditions used by the medical equipment may be read.

For example, the CT equipment may load a plurality of scanning conditions generated and stored by the equipment previously and may parse the information within the scanning conditions. The CT equipment may then acquire the information on the usage count, the execution time of the air calibration and the like in the scanning conditions.

In the block 203, the read scanning conditions may be selected sequentially in descending order of the usage count.

For example, the CT equipment may acquire the information on the usage count and the like included in the scanning conditions and may sort the plurality of scanning conditions in descending order according to the usage count. By sorting, the scanning condition pertaining to the usage count of which is larger may be preferentially selected as the preheating condition in the following blocks, so as to be more useful.

In the block 204, it may be determined whether the selected scanning condition meets an equipment calibration condition.

For example, in the present example the air calibration is exemplified. The equipment calibration condition may be that the time interval from the last execution time of the air calibration to the current time reaches 7 days. Therefore, it may be determined in this block whether the air calibration corresponding to the scanning condition has been performed during 7 days. For example, the latest execution time of the air calibration may be acquired from the selected scanning conditions and it may then be determined whether the time interval from the execution time to the current time reaches a pre-set threshold, e.g., 7 days.

If the determination result is that the time interval does not reach the pre-set threshold, for example, if the air calibration has been performed during 7 days, then it may indicate that the air calibration temporarily may not need to be performed. That is, the scanning condition does not meet the equipment calibration condition and may not be used as the preheating condition, and it continues to be determined whether the next scanning condition meets the equipment calibration condition. If the determination result is that the time interval reaches the pre-set threshold, for example, if the air calibration has not been performed during 7 days, then it may indicate that the scanning condition meets the equipment calibration condition and the following block 205 may then be performed.

In the block 205, the selected scanning condition meeting the equipment calibration condition may be determined as the preheating condition.

In the block 206, the estimation of the thermal capacity may be performed and it may be determined whether the accumulated thermal capacity according to all the determined preheating conditions may reach the target thermal capacity for the bulb tube preheating.

For example, every time a scanning condition may be determined as the preheating condition, the CT equipment may then perform this block of the method to determine whether the target thermal capacity required by the bulb tube preheating may be reached if the bulb tube preheating is performed in accordance with all the selected preheating conditions.

If the determination result of the block 206 is no, then it may indicate that the number of the selected preheating conditions may still be insufficient to complete the bulb tube preheating, and the block 207 may be performed to continue to determine whether all the read scanning conditions have been processed. If the determination result of the block 207 is no, then the process may be returned to perform the block 204 in order to continue to select the preheating condition which may be used for preheating the bulb tube from the scanning conditions used by the medical equipment. For example, it may continue to be determined whether the next scanning condition meets the equipment calibration condition in descending order of the usage count of the scanning conditions. On the other hand, if the determination result of the block 206 is yes, then it may indicate that the number of the preheating conditions selected by now has been sufficient to complete the bulb tube preheating and the following block 210 is to be directly performed.

In the present example, if the determination result of the block 207 is yes, it may indicate that the target thermal capacity still may not be reached after the analysis of all the scanning conditions is completed. Then, the process of the following block 208 may be performed.

In the block 208, the preheating condition preconfigured by the control system may be selected.

For example, the preconfigured preheating condition may be the preheating condition configured by the control system of the CT equipment originally.

In the block 209, the estimation of the thermal capacity may be performed in a similar manner to that in the block 206 and it may be determined whether the accumulated thermal capacity according to all the determined preheating conditions may reach the target thermal capacity for the bulb tube preheating.

For example, in the present example, when the preheating conditions selected according to the used scanning conditions may be insufficient to reach the target thermal capacity for the bulb tube preheating, the preheating condition configured by the control system originally may be added, until the target thermal capacity for the bulb tube preheating is reached.

If the determination result of the block 209 is that the target thermal capacity may not be reached, then the process may return to perform the block 208 in order to continue to add a next preheating condition preconfigured by the control system. If the determination result of the block 209 is that the target thermal capacity may be reached, then the following block 210 may be performed.

It should be noted that, the preheating condition preconfigured by the control system may be directly determined as the preheating condition. And when the bulb tube preheating may be performed by using the preheating condition preconfigured by the control system, the corresponding equipment calibration process may not be performed and the following block 210 may be referred to for the details.

In the block 210, the bulb tube preheating may be performed according to all the determined preheating conditions.

For example, after a plurality of preheating conditions may be determined, the bulb tube preheating may be performed according to each of the preheating conditions, and the preheating may be differently handled according to whether the determined preheating condition is a preheating condition determined according to the scanning condition or a preheating condition preconfigured by the control system.

For example, if the preheating condition is selected from the used scanning conditions, then the equipment calibration may be performed according to the scanning condition corresponding to the preheating condition; if the preheating condition is the preheating condition preconfigured by the control system, then the bulb tube preheating operation may be performed according to the preheating condition.

In one example, if the equipment calibration is the air calibration, then a slice may be opened to perform the air scanning according to the preheating condition, so as to generate the air calibration data under the scanning condition. In this case, when the bulb tube preheating is performed according to the preheating condition preconfigured by the control system, the slice opened when the air calibration is performed may also be closed, so as to ensure the efficiency of the bulb tube preheating as much as possible.

Corresponding to the method for preheating a bulb tube of the present disclosure, the present disclosure further provides an example for the medical equipment.

Figure 3:
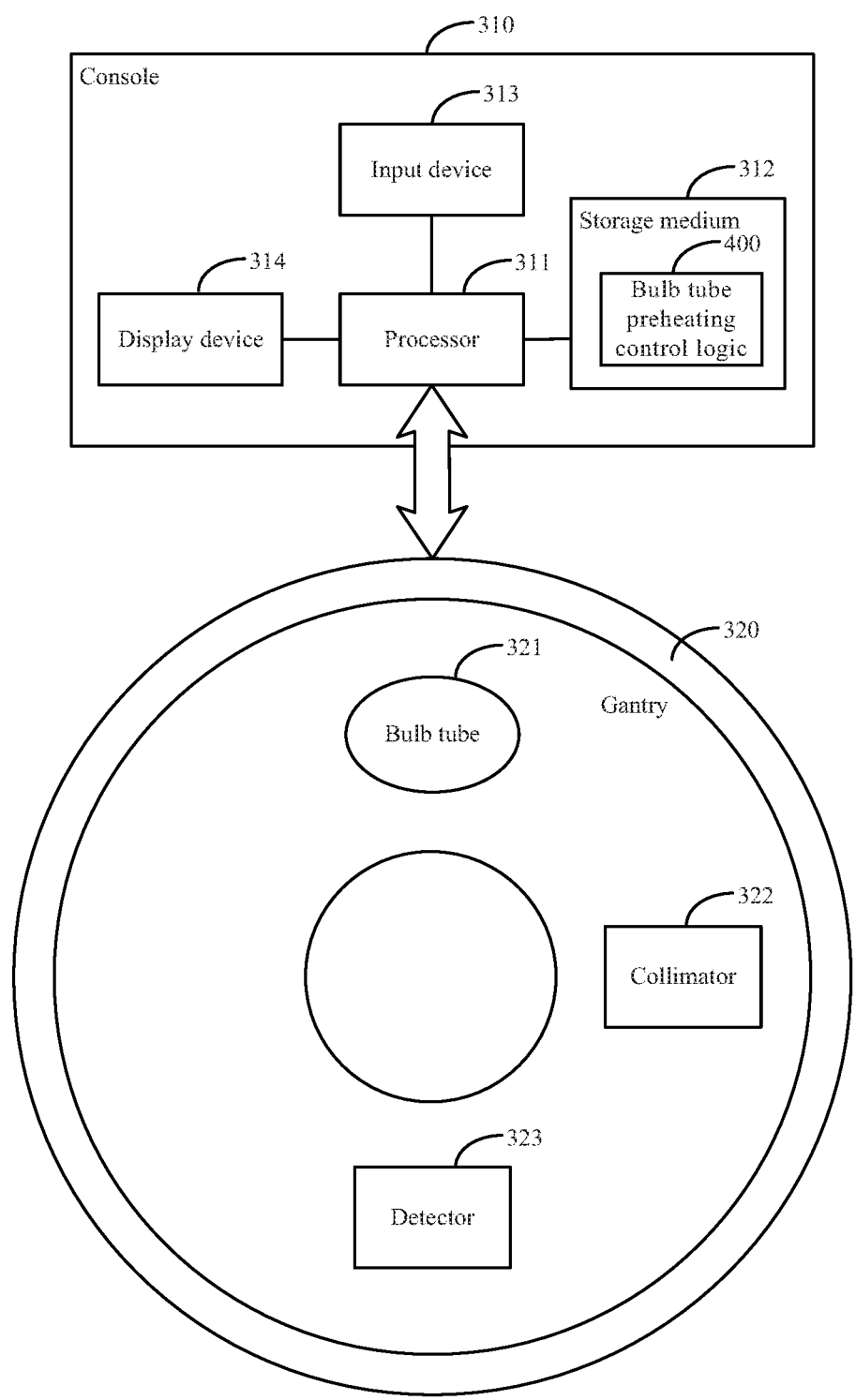
FIG. 3 is a schematic diagram of a hardware structure of an apparatus for preheating a bulb tube according to an example of the present disclosure.

As shown in FIG. 3, a schematic diagram of the system architecture of the medical equipment of the present disclosure is provided. Taking the CT equipment as an example of the medical equipment, the medical equipment may include a console 310 and a gantry 320. The console 310 may include a processor 311, a storage medium 312, an input device 313 and a display device 314, and the like. The gantry 320 may include a bulb tube 321 used as an X-ray source for example, a collimator 322, a detector 323, and the like. As one example, machine executable instructions corresponding to a bulb tube preheating control logic 400 may be stored in the storage medium 312. In different examples, the storage medium 312 may be a ROM (Read Only Memory), a volatile memory, a nonvolatile memory, a flash memory, a storage drive (such as a hard disk drive), a solid state drive, any type of storage disk (such as an optical disk, a DVD, etc.) or a similar storage medium, or a combination thereof.

When the bulb tube preheating is to be performed, the following operations may be executed by reading the machine executable instructions corresponding to the bulb tube preheating control logic 400 from the storage medium 312 by the processor 311.

A scanning condition may be selected from the scanning conditions used by the medical equipment, as a preheating condition for preheating the bulb tube of the medical equipment, wherein the selected scanning condition satisfies an equipment calibration condition.

In a case where accumulated thermal capacity according to all the selected preheating conditions is smaller than a target thermal capacity, a new preheating condition may be selected until the accumulated thermal capacity according to all the selected preheating conditions reaches the target thermal capacity. It will be appreciated that the accumulated thermal capacity may refer to a sum of the thermal capacity which may be estimated to be generated when the bulb tube is preheated according to each of the preheating conditions, and the target thermal capacity may represent a thermal capacity required to complete the bulb tube preheating.

The bulb tube of the medical equipment may be preheated according to all the selected preheating conditions and the equipment calibration corresponding to each of the preheating conditions may be performed during the process of the bulb tube preheating.

According to an example, when selecting a scanning condition from the scanning conditions used by the medical equipment as the preheating condition for preheating the bulb tube of the medical equipment, the processor 311 may be further caused by the machine executable instructions in the storage medium 312 to perform the following operations: acquiring the latest execution time of an equipment calibration corresponding to a scanning condition included in the scanning conditions used by the medical equipment; if a time interval from the latest execution time of the equipment calibration to the current time reaches a pre-set threshold, then determining that the scanning condition meets the equipment calibration condition; and selecting the scanning condition as the preheating condition.

According to an example, when selecting a scanning condition from the scanning conditions used by the medical equipment as a preheating condition for preheating the bulb tube of the medical equipment, the processor 311 may be further caused by the machine executable instructions in the storage medium 312 to perform the following operations: determining whether each of the scanning conditions meets the equipment calibration condition in a descending order of usage counts of all the scanning conditions.

According to an example, when continuing to select a new preheating condition in a case where the accumulated thermal capacity according to all the selected preheating conditions is smaller than the target thermal capacity, until the accumulated thermal capacity according to all the selected preheating conditions reaches the target thermal capacity, the processor 311 may be further caused by the machine executable instructions in the storage medium 312 to perform the following operations:

continuing to select a new preheating condition from the scanning conditions used by the medical equipment in a case where the accumulated thermal capacity according to all the selected preheating conditions is smaller than the target thermal capacity;

continuing to select a new preheating condition from preheating conditions preconfigured by a control system of the medical equipment if all the scanning conditions used by the medical equipment have been processed but the accumulated thermal capacity according to all the selected preheating conditions is still smaller than the target thermal capacity, until the accumulated thermal capacity according to all the selected preheating conditions reaches the target thermal capacity.

According to an example, when preheating the bulb tube of the medical equipment according to all the selected preheating conditions and executing an equipment calibration corresponding to each of the preheating conditions in the process of the bulb tube preheating, the processor 311 may be further caused by the machine executable instructions in the storage medium 312 to perform the following operations: performing an equipment calibration corresponding to the preheating condition on the medical equipment if the preheating condition is a scanning condition used by the medical equipment; preheating the bulb tube of the medical equipment if the preheating condition is a preheating condition preconfigured by the control system of the medical equipment.

Figure 4:
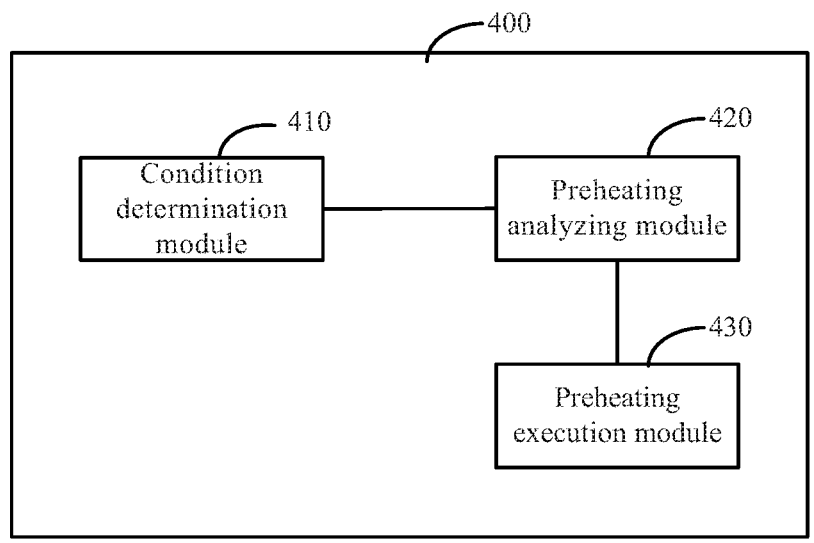
FIG. 4 is a schematic diagram of functional modules of control logic for preheating a bulb tube according to an example of the present disclosure.

The machine executable instructions corresponding to the bulb tube preheating control logic 400 may be stored on the storage medium 312. Referring to FIG. 4, the bulb tube preheating control logic may include a condition determination module 410, a preheating analyzing module 420 and a preheating execution module 430.

The condition determination module 410 may be used for selecting a scanning condition from a plurality of used scanning conditions as a preheating condition for preheating the bulb tube of the medical equipment, wherein the selected scanning condition may satisfy an equipment calibration condition.

The preheating analyzing module 420 may be used for determining whether accumulated thermal capacity of all the selected preheating conditions reaches a target thermal capacity. The preheating analyzing module 420 may cause the condition determination module 410 to continue to select a new preheating condition in the case where the accumulated thermal capacity may be smaller than the target thermal capacity, until the preheating analyzing module 420 determines that the accumulated thermal capacity of all the selected preheating conditions reaches the target thermal capacity. The target thermal capacity may be a thermal capacity required to complete the bulb tube preheating, and the accumulated thermal capacity may be a sum of the thermal capacity which may be estimated to be generated when the bulb tube preheating is performed according to each of the preheating conditions.

The preheating execution module 430 may be used for performing the bulb tube preheating according to all the preheating conditions and executing the equipment calibration corresponding to each of the preheating conditions in the process of the bulb tube preheating.

Further, when selecting the scanning condition from the scanning conditions used by the medical equipment as the preheating condition for preheating the bulb tube, the condition determination module 410 may specifically perform the following operations: acquiring the latest execution time of an equipment calibration corresponding to a scanning condition included in the scanning conditions used by the medical equipment; if a time interval from the latest execution time of the equipment calibration to the current time reaches a preset threshold, then determining that the scanning condition meets the equipment calibration condition and the scanning condition may be determined as the preheating condition.

Figure 5:
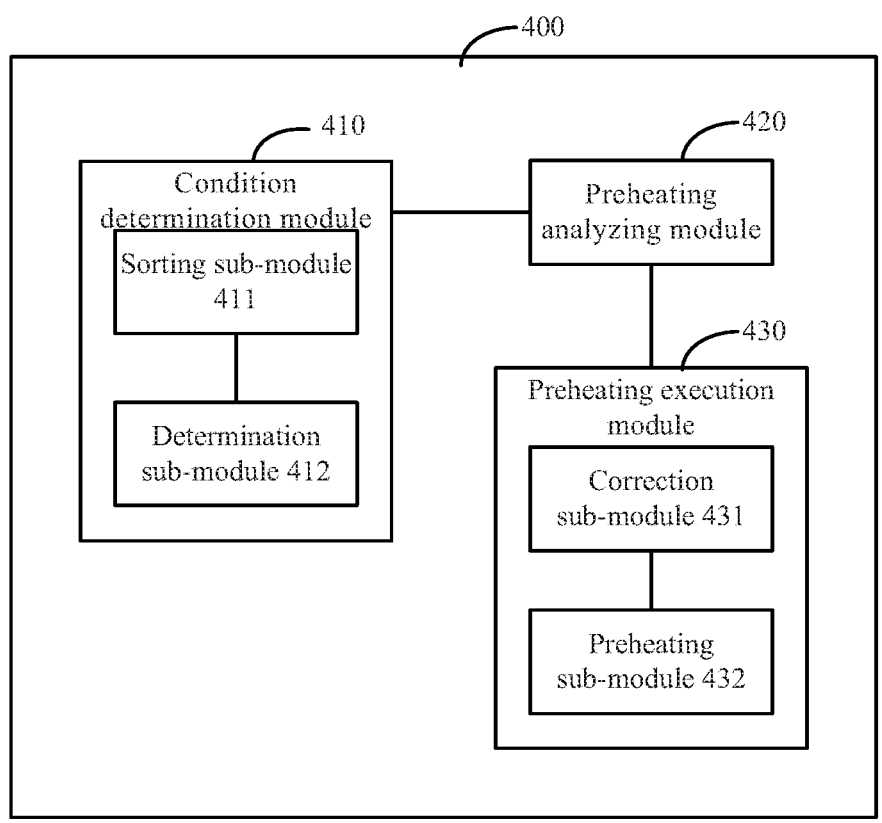
FIG. 5 is a schematic diagram of functional modules of control logic for preheating a bulb tube according to another example of the present disclosure.

According to an example, referring to FIG. 5, the condition determination module 410 may include a sorting sub-module 411 and a determination sub-module 412. The sorting sub-module 411 may be used for sorting the plurality of scanning conditions in a descending order of the usage counts. The determination sub-module 412 may be used for determining whether each of the scanning conditions used by the medical equipment meets the equipment calibration condition in the descending order of the usage counts of the scanning conditions.

Furthermore, the preheating analyzing module 420 may further be used for, when it is determined that the target thermal capacity still may not be reached according to all of the preheating conditions determined by the condition determination module 410, continuing to select a preheating condition preconfigured by the control system until the target thermal capacity is reached.

According to another example, as shown in FIG. 5, the preheating execution module 430 may include a calibration sub-module 431 and a preheating sub-module 432. Wherein, the calibration sub-module 431 may be used for performing the equipment calibration corresponding to the scanning condition, for example, opening a slice to performing the air scan, when the preheating condition is the used scanning condition; and the preheating sub-module 432 may be used for performing the bulb tube preheating, inclusive for example, of closing the slice opened when performing the equipment calibration, when the preheating condition is the preheating condition preconfigured by the control system.

The realization procedure of the corresponding blocks in the above method may be specifically referred to for the details of the realization procedure of the functions and roles of the above respective modules, which will not be repeated here.

The above are only preferred examples of the present disclosure is not intended to limit the disclosure within the spirit and principles of the present disclosure, any changes made, equivalent replacement, or improvement in the protection of the present disclosure should be contained within the range of the present disclosure.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product may be stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example may be arranged in the device in the examples as described, or may be alternatively located in one or more devices different from that in the examples. The units in the examples described may be combined into one module or may be further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or block, or group of elements, integers or blocks, but not the exclusion of any other element, integer or block, or group of elements, integers or blocks.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for preheating a bulb tube of medical equipment, comprising:
   reading a target thermal capacity which represents a thermal capacity required to complete preheating of the bulb tube of the medical equipment;
   selecting a scanning condition from scanning conditions used by the medical equipment as a preheating condition for preheating the bulb tube of the medical equipment, wherein the selected scanning condition satisfies an equipment calibration condition and an equipment calibration corresponding to the equipment calibration condition is to be executed when the preheating condition is reached;
   continuing to select a new preheating condition until an accumulated thermal capacity reaches the target thermal capacity, wherein the accumulated thermal capacity refers to a sum of a thermal capacity which is estimated to be generated when the bulb tube is preheated according to each of the selected preheating conditions; and
   preheating the bulb tube of the medical equipment according to the selected preheating conditions so as to obtain calibration data of the equipment calibration corresponding to each of the preheating conditions.

2. The method according to claim 1, wherein said selecting the scanning condition from the scanning conditions used by the medical equipment as the preheating condition for preheating the bulb tube of the medical equipment includes:
   acquiring a latest execution time of an equipment calibration corresponding to the scanning condition included in the scanning conditions used by the medical equipment;
   determining that the scanning condition meets the equipment calibration condition and selecting the scanning condition as the preheating condition if a time interval from the latest execution time of the equipment calibration to a current time reaches a preset threshold.

3. The method according to claim 1, wherein said selecting the scanning condition from the scanning conditions used by the medical equipment as the preheating condition for preheating the bulb tube of the medical equipment, includes:
   determining whether each of the scanning conditions used by the medical equipment meets the equipment calibration condition in a descending order of usage counts of the scanning conditions.

4. The method according to claim 1, wherein said continuing to select a new preheating condition in a case where the accumulated thermal capacity according to the selected preheating conditions is smaller than the target thermal capacity, until the accumulated thermal capacity according to the selected preheating conditions reaches the target thermal capacity, includes:
   continuing to select the new preheating condition from the scanning conditions used by the medical equipment in the case where the accumulated thermal capacity according to the selected preheating conditions is smaller than the target thermal capacity;
   continuing to select the new preheating condition from preheating conditions preconfigured by a control system of the medical equipment under a condition that the scanning conditions used by the medical equipment have been processed but the accumulated thermal capacity according to the selected preheating conditions is still smaller than the target thermal capacity, until the accumulated thermal capacity according to the selected preheating conditions reaches the target thermal capacity.

5. The method according to claim 4, wherein said preheating the bulb tube of the medical equipment according to the selected preheating conditions so as to obtain calibration data of the equipment calibration corresponding to each of the preheating conditions includes:

obtaining the calibration data by performing an equipment calibration corresponding to the preheating condition on the medical equipment if the preheating condition is the scanning condition used by the medical equipment; and preheating the bulb tube of the medical equipment if the preheating condition is the preheating condition preconfigured by the control system of the medical equipment.

6. An apparatus for preheating a bulb tube of medical equipment, comprising a processor, by reading and executing machine executable instructions corresponding to a bulb tube preheating control logic, which are stored on a machine readable storage medium, the processor being caused by the machine executable instructions to:

read a target thermal capacity which represents a thermal capacity required to complete preheating of the bulb tube of the medical equipment;

select a scanning condition from scanning conditions used by the medical equipment as a preheating condition for preheating the bulb tube of the medical equipment, wherein the selected scanning condition satisfies an equipment calibration condition and an equipment calibration corresponding to the equipment calibration condition is to be executed when the preheating condition is reached;

continue to select a new preheating condition until an accumulated thermal capacity reaches the target thermal capacity, wherein the accumulated thermal capacity refers to a sum of a thermal capacity which is estimated to be generated when the bulb tube is preheated according to each of the selected preheating conditions; and preheat the bulb tube according to the selected preheating conditions so as to obtain calibration data of the equipment calibration corresponding to each of the preheating conditions.

7. The apparatus according to claim 6, wherein when selecting the scanning condition from the scanning conditions used by the medical equipment as the preheating condition for preheating the bulb tube of the medical equipment, the processor is caused by the machine executable instructions to:

acquire a latest execution time of an equipment calibration corresponding to the scanning condition included in the scanning conditions used by the medical equipment;

determine that the scanning condition meets the equipment calibration condition and select the scanning condition as the preheating condition if a time interval from the latest execution time of the equipment calibration to a current time reaches a preset threshold.

8. The apparatus according to claim 6, wherein when selecting the scanning condition from the scanning conditions used by the medical equipment as the preheating condition for preheating the bulb tube of the medical equipment, the processor is caused by the machine executable instructions to:

determine whether each of the scanning conditions used by the medical equipment meets the equipment calibration condition in a descending order of usage counts of the scanning conditions.

9. The apparatus according to claim 6, wherein when continuing to select a new preheating condition in a case where the accumulated thermal capacity according to the selected preheating conditions is smaller than the target thermal capacity, until the accumulated thermal capacity according to the selected preheating conditions reaches the target thermal capacity, the processor is caused by the machine executable instructions to:

continue to select the new preheating condition from the scanning conditions used by the medical equipment in the case where the accumulated thermal capacity according to the selected preheating conditions is smaller than the target thermal capacity;

continue to select the new preheating condition from preheating conditions preconfigured by a control system of the medical equipment under a condition that the scanning conditions used by the medical equipment have been processed but the accumulated thermal capacity according to the selected preheating conditions is still smaller than the target thermal capacity, until the accumulated thermal capacity according to the selected preheating conditions reaches the target thermal capacity.

10. The apparatus according to claim 9, wherein when preheating the bulb tube of the medical equipment according to the selected preheating conditions so as to obtain calibration data of the equipment calibration corresponding to each of the preheating conditions, the processor is caused by the machine executable instructions to:

obtain the calibration data by performing an equipment calibration corresponding to the preheating condition on the medical equipment if the preheating condition is a scanning condition used by the medical equipment; and preheat the bulb tube of the medical equipment if the preheating condition is a preheating condition preconfigured by the control system of the medical equipment.

* * * * *